United States Patent [19]

Schmidt

[11] 4,248,723

[45] Feb. 3, 1981

[54] ACETAL DERIVATIVES AS EXTREME PRESSURE ADDITIVES FOR LUBRICANTS

[75] Inventor: Andreas Schmidt, Reinach, Switzerland

[73] Assignee: Ciba-Geigy Corporation, Ardsley, N.Y.

[21] Appl. No.: 915,624

[22] Filed: Jun. 14, 1978

[30] Foreign Application Priority Data

Jun. 23, 1977 [CH] Switzerland .......... 7721/77

[51] Int. Cl.³ .......... C10M 1/38
[52] U.S. Cl. .......... 252/48.6; 560/147; 560/152; 560/154
[58] Field of Search .......... 252/48.2, 48.6; 560/147, 152, 154

[56] References Cited

U.S. PATENT DOCUMENTS

| | | | |
|---|---|---|---|
| 2,520,748 | 8/1950 | Vaughan et al. | 252/48.2 |
| 2,522,476 | 9/1950 | Wasson | 252/48.6 |
| 2,543,325 | 2/1951 | Mattson | 252/48.6 X |
| 2,580,695 | 1/1952 | Niederhauser | 260/608 X |
| 2,874,192 | 2/1959 | Cottle et al. | 252/48.6 X |
| 3,296,137 | 1/1967 | Wiese | 252/48.2 |
| 3,314,888 | 4/1967 | Matson | 252/48.6 |
| 3,494,947 | 2/1970 | Schutze et al. | 560/154 |
| 3,501,520 | 3/1970 | Giolito | 560/154 |
| 4,042,514 | 8/1977 | Giolito | 252/48.6 |

FOREIGN PATENT DOCUMENTS

1371949 10/1974 United Kingdom .......... 252/47

OTHER PUBLICATIONS

Evans Chemetics, Inc., Chem. & Engineering News, Apr. 5, 1971, p. 5.

Primary Examiner—Andrew Metz
Attorney, Agent, or Firm—Harry Falber

[57] ABSTRACT

Acetal and thioacetal derivatives of the formula I

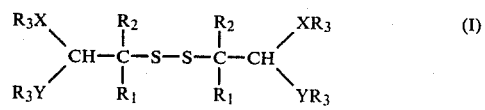

in which $R_1$ and $R_2$ are identical or different $C_1$-$C_{12}$ alkyl or together are $C_4$-$C_7$ alkylene, X and Y are identical or different and are each O or S and $R_3$ is $C_1$-$C_{18}$ alkyl, $C_6$-$C_{18}$ aryl, $C_7$-$C_9$ aralkyl, carboxy-($C_1$-$C_2$)-alkyl, ($C_1$-$C_{18}$-alkoxy)-carbonyl-($C_1$-$C_2$)-alkyl, N-$C_1$-$C_{18}$-alkylated carbamoyl-($C_1$-$C_2$)-alkyl or an ammonium salt of an amine with carboxymethyl or 2-carboxyethyl, or two $R_3$ radicals of an acetal/thioacetal group together are $C_2$-$C_4$ alkylene.

6 Claims, No Drawings

ACETAL DERIVATIVES AS EXTREME PRESSURE ADDITIVES FOR LUBRICANTS

The present invention relates to acetal and thioacetal derivatives and their use as additives for lubricants and also to the lubricating oil formulations provided with the novel compounds.

Various additives are generally added to mineral and synthetic lubricants in order to improve their characteristics in use. In particular, there is a need for additives which are intended to protect the devices to be lubricated from wear due to friction. The demands made upon such wear inhibitors are that they increase the load-bearing capacity of the lubricant and do not have a corrosive action on the metal parts to be protected. Known additives for lubricants are sulphurised sperm oil and sulphurised olefins, for example according to German Offenlegungsschrift No. 2,166,893 and German Offenlegungsschrift No. 2,606,101. The extreme-pressure characteristics of lubricants containing such additives are frequently not satisfactory.

Surprisingly, it has now been found that the acetal and thioacetal derivatives of the formula I are superior to the known extreme-pressure additives for lubricants, especially when employed in relatively low concentrations, in respect of the stability to heat, non-corrosivity towards iron and nonferrous metals and resistance to hydrolysis.

The invention accordingly relates to acetal and thioacetal derivatives of the formula I

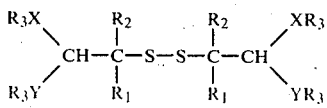

in which $R_1$ and $R_2$ are identical or different $C_1$–$C_{12}$ alkyl or together are $C_4$–$C_7$ alkylene, X and Y are identical or different and are each O or S and $R_3$ is $C_1$–$C_{18}$ alkyl, $C_6$–$C_{18}$ aryl, $C_7$–$C_9$ aralkyl, carboxy-($C_1$–$C_2$)-alkyl, ($C_1$–$C_{18}$-alkoxy)-carbonyl-($C_1$–$C_2$)-alkyl, N-$C_1$–$C_{18}$-alkylated carbamoyl-($C_1$–$C_2$)-alkyl or an ammonium salt of an amine with carboxymethyl or 2-carboxyethyl, or two $R_3$ radicals of an acetal/thioacetal group together are $C_2$–$C_4$ alkylene.

Alkyl $R_1$ and $R_2$ is straight-chain or branched alkyl having 1–12 C atoms, such as n-propyl, i-propyl, n-butyl, i-butyl, sec.-butyl, amyl, neopentyl, hexyl, 1-methylpentyl, n-octyl, i-octyl, t-octyl, 2-ethyl-hexyl, n-decyl, 2-ethyl-decyl and n-dodecyl, especially ethyl and in particular methyl.

Alkylene $R_1/R_2$ is especially tetramethylene or pentamethylene and alkylene $R_1/R_2$ is bonded to the same C atom which carries these radicals $R_1/R_2$.

Alkyl $R_3$ is in particular alkyl as defined for $R_1$ and $R_2$. Aryl $R_3$ is in particular phenyl or alkylphenyl in which alkyl in particular has 1–12 C atoms and preferably has the meaning defined for $R_1$, such as methylphenyl. Aralkyl $R_3$ is in particular benzyl and carboxyalkyl $R_3$ is in particular carboxymethyl or 2-carboxyethyl. Alkoxycarbonylalkyl $R_3$ is, for example, alkoxycarbonylmethyl or 2-alkoxycarbonylethyl in which the alkyl moiety in alkoxy in particular has the meaning defined for $R_1$, such as octyloxycarbonylmethyl. N-Alkylated carbamoylalkyl is in particular N-alkylated carbamoylmethyl or carbamoylethyl in which 1 or 2 alkyl groups, in particular having up to 18 C atoms, can be bonded to N, such as N-dodecylcarbamoylmethyl or N-tetradecylcarbamoylmethyl, or in which alkylene, such as $C_4$–$C_6$ alkylene, is bonded to N, for example piperidinocarbonylmethyl. An ammonium salt of an amine with carboxymethyl or carboxyethyl is in particular such an ammonium salt with a primary, secondary or tertiary amine, such as a $C_1$–$C_{18}$ alkylamine, di-($C_1$–$C_{18}$)-alkylamine, tri-($C_1$–$C_{18}$)-alkylamine or $C_2$–$C_{18}$ alkylenediamine, or with a cyclic amine, such as pyrrolidine or piperidine, for example methylamine, dodecylamine, dimethylamine, di-n-octylamine, trimethylamine, triethylamine, tridodecylamine, 1,3-diaminopropane and the like. Alkylene formed by two groups $R_3$ is in particular ethylene.

Preferred acetal and thioacetal derivatives of the formula I are those in which $R_1$ and $R_2$ are identical or different $C_1$–$C_{12}$ alkyl, X and Y are identical or different and are each O or S and $R_3$ is $C_1$–$C_{18}$ alkyl, $C_6$–$C_{18}$ aryl, $C_7$–$C_9$ aralkyl, ($C_1$–$C_{18}$-alkoxy)-carbonylmethyl or 2-($C_1$–$C_{18}$-alkoxy)-carbonyl-ethyl, or two $R_3$ radicals of an acetal/thioacetal group together are $C_2$–$C_4$ alkylene.

Particularly preferred acetal and thioacetal derivatives of the formula I are those in which $R_1$ and $R_2$ are methyl, X and Y are S and $R_3$ is $C_1$–$C_{18}$ alkyl or ($C_1$–$C_{18}$-alkoxy)-carbonylmethyl.

The compounds illustrated in the examples are also particularly preferred.

The acetal and thioacetal derivatives of the formula I can be prepared by methods known per se. Thus, the corresponding aldehyde or thiaaldehyde $X=CH-CR_1R_2-SS-CR_1R_2-CH=X$ can be used as the starting material and reacted with a compound $R_3XH$. The reaction is preferably carried out using a catalyst, especially an acid catalyst, such as a sulphonic acid, for example toluenesulphonic acid, or active bleaching earth, for example Tonsil AC. The starting aldehydes and thiaaldehydes are known, for example from U.S. Pat. No. 2,580,695, or, if they are novel, can be prepared analogously to the known compounds.

In resulting compounds of the formula I which have free carboxyl groups, these groups can be converted to carbamoyl groups in a manner known per se, for example by reacting such compounds with an alkylamine.

Even in every small amounts, the compounds of the formula I are effective as extreme-pressure additives in lubricants. Thus, mineral and synthetic lubricating oils, and also mixtures thereof, which are provided with 0.001 to 5% by weight, and preferably 0.02 to 3%, based on the lubricant, of a compound of the formula I display excellent extreme-pressure lubricating properties which manifest themselves in greatly reduced wear phenomena of the parts which undergo friction against one another and are to be lubricated. The lubricants are commonly known to those skilled in the art and are described, for example, in "Schmiermittel Taschenbuch" ("Lubricants Handbook") (Hüthig Verlag, Heidelberg, 1974).

The lubricating oil formulation can additionally also contain other additives, which are added in order to improve certain characteristics in use, such as antioxidants, metal passivators, rust inhibitors, viscosity index improvers, pour point depressors, dispersants/detergents and other wear resisting additives.

Examples of antioxidants are:

(a) Alkylated and non-alkylated aromatic amines and mixtures thereof, for example: dioctyldiphenylamine, mono-t-octyl-phenyl-α- and -β-naphthylamine, phenotriazine, dioctylphenothiazine, phenyl-α-naphthylamine and N,N'-di-sec.-butyl-p-phenylenediamine.

(b) Sterically hindered phenols, for example 2,6-ditert.-butyl-p-cresol, 4,4'-bis-(2,6-diisopropylphenol), 2,4,6-tri-isopropylphenol, 2,2'-thio-bis-(4-methyl-6-tert.-butylphenol) and 4,4'-methylene-bis-(2,6-di-tert.-butylphenol).

(c) Alkyl phosphites, aryl phosphites or alkaryl phosphites, for example: trinonyl phosphite, triphenyl phosphite and diphenyl decyl phosphite.

(d) Esters of thiodipropionic acid or thiodiacetic acid, for example: dilauryl thiodipropionate or dioctyl thiodiacetate.

(e) Salts of carbamic and dithiophosphoric acids, for example: antimony diamyldithiocarbamate and zinc diamyldithiophosphate.

(f) A combination of two or more antioxidants from amongst the above, for example: an alkylated amine and a sterically hindered phenol.

Examples of metal passivators are:

(a) for copper, for example benzotriazole, tetrahydrobenzotriazole, 2-mercaptobenzotriazole, 2,5-dimercaptothiadiazole, salicylidene-propylenediamine and salts of salicylaminoguanidine.

(b) for lead, for example sebacic acid derivatives, quinizarine and propyl gallate, and (c) a combination of two or more of the above additives.

Examples of rust inhibitors are:

(a) Organic acids and their esters, metal salts and anhydrides, for example: N-oleyl-sarcosine, sorbitane monooleate, lead naphthenate and dodecenylsuccinic anhydride.

(b) Nitrogen-containing compounds, for example:

I. Primary, secondary or tertiary aliphatic or cycloaliphatic amines and amine salts of organic and inorganic acids, for example oil-soluble alkylammonium carboxylates.

II. Heterocyclic compounds, for example: substituted imidazolines and oxazolines.

(c) Phosphorus-containing compounds, for example: amine salts of phosphoric acid partial esters, (d) Sulphur-containing compounds, for example: barium dinonylnaphthalene-sulphonates and calcium petroleum-sulphonates, and (e) Combinations of two or more of the above additives.

Examples of viscosity index improvers are: polymethacrylates, vinylpyrrolidone/methacrylate copolymers, polybutenes, olefin copolymers and styrene/acrylate copolymers.

Examples of pour point depressors are: polybutenylsuccinic acid imides, polybutenylphosphonic acid derivatives and hyperbasic magnesium, calcium and barium sulphonates and phenolates.

Examples of other wear resisting additives are: compounds containing sulphur and/or phosphorus and/or halogen, such as sulphurised vegetable oils, zinc dialkyldithiophosphates, tritolyl phosphate, chlorinated paraffins, alkyl disulphides and aryl disulphides.

The examples which follow illustrate the invention.

EXAMPLE 1

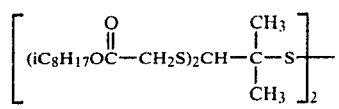

20.6 g (0.1 mol) of 2,2'-dithio-bis-[2-methyl]-propanal, 81.7 g (0.4 mol) of 2-ethylhexyl thioglycollate and 2 g of Tonsil AC (active bleaching earth from Süd-Chemie, Germany) are refluxed in 50 ml of hexane for 2 hours, with stirring, under a water separator. 3.6 ml of water split off. The reaction mixture is filtered to remove the Tonsil and is then concentrated completely under reduced pressure. This yields 98 g of the di-thioacetal in the form of a virtually colourless oil. (Additive No. 1).

EXAMPLE 2

Replacing the isooctyl thioglycollate in Example 1 by the equimolar amount of thioglycollic acid and otherwise following an identical procedure yields the corresponding dithioacetal.

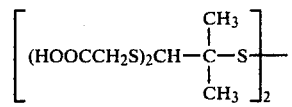

(Additive No. 2).

EXAMPLE 3

20.6 g (0.1 mol) of 2,2'-dithio-bis-[2-methyl]-propanal, 81 g (0.4 mol) of tert.-dodecylmercaptan and 1 g of 4-toluenesulphonic acid are refluxed in 150 ml of hexane for 3½ hours, with stirring, under a water separator. The reaction mixture is then cooled and washed, first with dilute sodium acetate solution and then with water, and the organic phase is concentrated completely under reduced pressure. This yields the dithioacetal in the form of a yellowish oil.

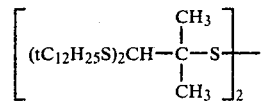

(Additive No. 3).

EXAMPLES 4–8

Replacing the tert.-dodecylmercaptan in Example 3 by the mercaptans listed in Table 1 and otherwise following an identical procedure yields the corresponding dithioacetals:

Table 1

| Additive No. (Ex. No.) | Mercaptan | End Product |
|---|---|---|
| 4 | n-C$_{12}$H$_{25}$SH | $\left[(nC_{12}H_{25}S)_2CH-\overset{\overset{CH_3}{|}}{\underset{\underset{CH_3}{|}}{C}}-S\right]_2$ |

Table 1-continued

| Additive No. (Ex. No.) | Mercaptan | End Product |
|---|---|---|
| 5 | n-$C_8H_{17}SH$ | $[(nC_8H_{17}S)_2CH-\underset{CH_3}{\overset{CH_3}{\underset{|}{\overset{|}{C}}}}-S-]_2$ |
| 6 | 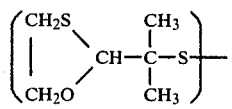 | $[(\text{Ph-S})_2CH-\underset{CH_3}{\overset{CH_3}{\underset{|}{\overset{|}{C}}}}-S-]_2$ |
| 7 | 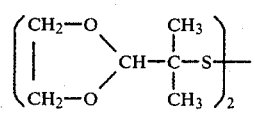 | $[(CH_3-\text{Ph-S})_2CH-\underset{CH_3}{\overset{CH_3}{\underset{|}{\overset{|}{C}}}}-S-]_2$ |
| 8 | Ph-$CH_2SH$ | $[(\text{Ph-}CH_2S)_2CH-\underset{CH_3}{\overset{CH_3}{\underset{|}{\overset{|}{C}}}}-S-]_2$ |

EXAMPLE 9

20.6 g (0.1 mol) of 2,2'-dithio-bis-[2-methyl]-propanal, 16 g (0.2 mol) of mercaptoethanol and 1 g of 4-toluene-sulphonic acid are refluxed in 150 ml of hexane for 10 hours, with stirring, under a water separator. The reaction mixture is then cooled and washed, first with dilute sodium acetate solution and then with water, and the organic phase is concentrated completely under reduced pressure. This yields the corresponding cyclic thioacetal in the form of a slightly reddish oil.

$$\left( \begin{array}{c} CH_2S \\ | \\ CH_2O \end{array} \right) CH-\underset{CH_3}{\overset{CH_3}{\underset{|}{\overset{|}{C}}}}-S \left. \right)$$

(Additive No. 9).

EXAMPLE 10

Replacing the mercaptoethanol in Example 9 by an equimolar amount of ethylene glycol and otherwise following an identical procedure yields the corresponding cyclic acetal.

$$\left( \begin{array}{c} CH_2-O \\ | \\ CH_2-O \end{array} \right) CH-\underset{CH_3}{\overset{CH_3}{\underset{|}{\overset{|}{C}}}}-S \left. \right)_2$$

(Additive No. 10).

EXAMPLE 11

13.3 g (0.025 mol) of additive No. 2 are dissolved in 50 ml of toluene and 19.1 g (0.1 mol) of Primene 81-R (a mixture of primary $C_{12}$–$C_{15}$ t.-alkylamines, Rohm and Haas, U.S.A.) are added, with stirring. The solvent is completely distilled off under reduced pressure. This yields a yellowish transparent oil (additive No. 11) which is readily soluble in hexane and mineral oil and is the N-alkylated ammonium salt corresponding to additive No. 2.

EXAMPLE 12

The exceptional load-bearing characteristics of the lubricant additives according to the invention are shown by tests in the gearwheel deformation test stand of the "Forschungsstelle für Zahnräder und Getriebe" (FZG).

For this purpose, mixtures of the additives according to the invention in a non-doped mineral lubricating oil (viscosity: 20 cSt/50° C.) were prepared and tested according to DIN 51,354 (Standard Test A/8.3/90) using the FZG machine. For comparison, the non-doped mineral lubricating oil was also tested without an additive, using the FZG machine.

The results of these tests are summarised in Table 2 below

Table 2

| Test No. | Additive No. | Concentration % by weight | Δms [mg/KWh] | Failure under load |
|---|---|---|---|---|
| 1 | none | — | 0.61 | 6–7 |
| 2 | 1 | 0.5 | 0.1 | 12 |

EXAMPLE 13

The following values were determined using the Shell four-ball apparatus: (Tentative method IP 239/69, Extreme pressure and wear lubricant test for oils and greases, four-ball machine).

(1) I.S.L. = Initial Seizure Load: that is the load under which the oil film collapses within a load period of 10 seconds.

(2) W.L. = Weld Load: that is the load under which the 4 balls weld together within 10 seconds.

(3) W.S.D. = Wear Scar Diameter in mm: that is the average wear diameter after subjection to a load of 40 kg for 1 hour.

Catenex 41 (Shell tradename) was used as the base oil.

The results of these tests are summarised in Table 3 below.

Table 3

| Additive No. | Concentration in % by weight | ISL (kg) | WL (kg) | WSD (mm) |
|---|---|---|---|---|
| none | — | 60 | 160 | 1.1 |
| 1 | 1% | 120 | 230 | 0.65 |
| 3 | 1% | 70 | 220 | 0.60 |
| 4 | 1% | — | >200 | 0.60 |
| 5 | 1% | — | >200 | 0.60 |
| 6 | 1% | — | >200 | 0.50 |
| 7 | 1% | — | >200 | 0.50 |
| 8 | 1% | — | >200 | 0.60 |
| 9 | 1% | 130 | 280 | 0.70 |
| 10 | 1% | 80 | 230 | 0.68 |
| 11 | 1% | 170 | 260 | 0.80 |

What is claimed is:

1. An acetal derivative of the formula I

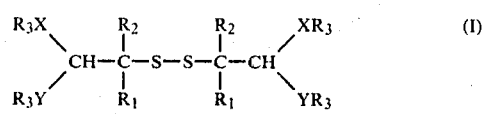

in which $R_1$ and $R_2$ are identical or different $C_1$–$C_{12}$ alkyl or together are $C_4$–$C_7$ alkylene, X and Y are each O and $R_3$ is ($C_1$–$C_{18}$-alkoxy)-carbonyl-($C_1$–$C_2$)-alkyl.

2. An acetal derivative according to claim 1, in which $R_1$ and $R_2$ are identical or different $C_1$–$C_{12}$ alkyl, X and Y are each O and $R_3$ is ($C_1$–$C_{18}$-alkoxy)-carbonylmethyl or 2-($C_1$–$C_{18}$-alkoxy)-carbonyl-ethyl.

3. An acetal derivative according to claim 1, in which $R_1$ and $R_2$ are methyl, X and Y are O and $R_3$ is ($C_1$–$C_{18}$-alkoxy)-carbonylmethyl.

4. An acetal derivative according to claim 1, which is 2,2'-dithio-bis-[2-methyl]-propanal tetra-(2-ethylhexyloxy-carbonylmethyl)-acetal.

5. A compound according to claim 1, of the formula

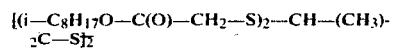

6. A lubricant composition comprising a major proportion of an oil of lubricating viscosity and in an amount to provide extreme pressure properties of the compound of claim 1.

* * * * *